United States Patent
Sugioka et al.

(10) Patent No.: US 7,745,666 B2
(45) Date of Patent: Jun. 29, 2010

(54) METHOD FOR PRODUCING ALDEHYDE USING BISPHOSPHITE AND GROUP 8-10 METAL COMPOUND, AND SUCH BISPHOSPHITE

(75) Inventors: Takashi Sugioka, Okayama (JP); Jin Tokuyasu, Tokyo (JP); Takuo Tsuruta, Okayama (JP); Hideharu Iwasaki, Okayama (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 0 days.

(21) Appl. No.: 12/295,874

(22) PCT Filed: Apr. 3, 2007

(86) PCT No.: PCT/JP2007/057492

§ 371 (c)(1),
(2), (4) Date: Oct. 3, 2008

(87) PCT Pub. No.: WO2007/114445

PCT Pub. Date: Oct. 11, 2007

(65) Prior Publication Data

US 2009/0259073 A1 Oct. 15, 2009

(30) Foreign Application Priority Data

Apr. 4, 2006 (JP) .............................. 2006-103164

(51) Int. Cl.
C07C 45/50 (2006.01)
C07F 9/02 (2006.01)
(52) U.S. Cl. ............................ 568/454; 568/12; 568/14
(58) Field of Classification Search ................ 568/454, 568/12, 14
See application file for complete search history.

(56) References Cited

U.S. PATENT DOCUMENTS

2002/0111487 A1 8/2002 Roettger et al.
2006/0058557 A1 3/2006 Peng et al.

FOREIGN PATENT DOCUMENTS

| EP | 1 008 581 A1 | 6/2000 |
|---|---|---|
| JP | 62 116535 | 5/1987 |
| JP | 04 290551 | 10/1992 |
| JP | 8 10624 | 1/1996 |
| JP | 11 292887 | 10/1999 |
| JP | 2002 193987 | 7/2002 |
| JP | 2006 503086 | 1/2006 |
| WO | WO 02/0670 A1 | 1/2002 |

OTHER PUBLICATIONS

Pruett, R. L. et al., "A Low-Pressure System for Producing Normal Aldehydes by Hydroformylation of Alpha Olefins[1]", Hydroformylation of Alpha Olefins, vol. 34, No. 2, pp. 327-330, (1969).

Van Rooy, Annemiek et al., "Hydroformylation of Oct-1-ene with Extremely High Rates using Rhodium Catalysts containing Bulky Phosphites", J. Chem. Soc., Chem. Commun., pp. 1096-1097, (1991).

Van Rooy, Annemiek et al., "Bulky Diphosphite-Modified Rhodium Catalysts: Hydroformylation and Characterization", Organometallics, vol. 15, No. 2, pp. 835-847, (1996).

Dieleman, Cedric B. et al., "Xantphite: A New Family of Ligands for Catalysis. Applications in the Hydroformylation of Alkenes", Helvetica Chimica Acta, vol. 84, pp. 3269-3280, (2001).

Rocco Paciello, et al., "Structure-activity relationship for chelating phosphite ligands used in rhodium-catalyzed hydroformylations", Journal of Molecular Catalysis A:Chemical, vol. 143, No. 1-3, XP-002499694, Jan. 1, 1999, pp. 85-97.

*Primary Examiner*—Sikarl A Witherspoon
(74) *Attorney, Agent, or Firm*—Oblon, Spivak, McClelland, Maier & Neustadt, L.L.P.

(57) ABSTRACT

A bisphosphite represented by the general formula (I):
General Formula (I)

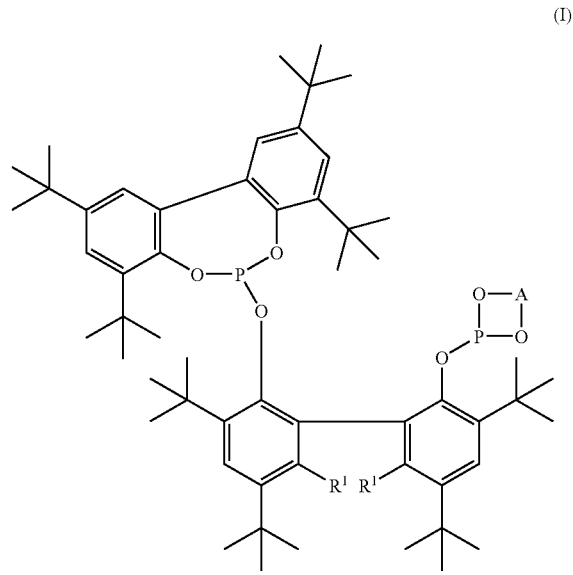

(in the formula, A represents an alkylene group which may have a substituent, a cycloalkylene group which may have a substituent, a phenylene group which may have a substituent, or a naphthylene group which may have a substituent; and $R^1$ represents a hydrogen atom or an alkyl group) and a method for producing an aldehyde including reacting a non-conjugated diene having a carbon-carbon double bond in a molecular end and having from 6 to 20 carbon atoms with a carbon monoxide and hydrogen in the presence of such a bisphosphite and a group 8 to 10 metal compound, are provided.

10 Claims, No Drawings

METHOD FOR PRODUCING ALDEHYDE USING BISPHOSPHITE AND GROUP 8-10 METAL COMPOUND, AND SUCH BISPHOSPHITE

TECHNICAL FIELD

The present invention relates to a method for producing an aldehyde comprising reacting a non-conjugated diene having a carbon-carbon double bond in an end thereof and having from 6 to 20 carbon atoms with carbon monoxide and hydrogen in the presence of a bisphosphite having a specified structure and a group 8 to 10 metal compound and to such a bisphosphite. The aldehyde obtained by the present invention is useful as a raw material for medical or pesticidal intermediates or various chemicals or the like.

BACKGROUND ART

A method for producing an aldehyde by reacting an olefinic compound with carbon monoxide and hydrogen in the presence of a group 8 to 10 metal compound or a group 8 to 10 metal compound and a phosphorus compound is called "hydroformylation reaction" or "oxo reaction", and it is well-known that this method is industrially extremely valuable as a method for producing an aldehyde.

In general, in such a hydroformylation reaction, a rhodium compound or a combination of a rhodium compound and a phosphorus compound is industrially used as a catalyst. As such a phosphorus compound, for example, phosphines such as tributylphosphine, trioctylphosphine, tricyclohexylphosphine, triphenylphosphine, tri(p-tolyl)phosphine, etc. (see, for example, Patent Document 1); monophosphites such as triphenylphosphite, tri-n-butylphosphite, tris(2-t-butyl-4-methylphenyl)phosphite, etc. (see, for example, Non-Patent Documents 1 and 2); bisphosphites such as bis[3,3',5,5'-tetra-t-butyl(1,1'-biphenyl)-2,2'-diyl]-1,2-ethyldiphosphite, bis[3,3',5,5'-tetra-t-butyl(1,1'-biphenyl)-2,2'-diyl]-2,7,9,9-tetramethyl-9H-xanthin-4,5-diyldiphosphite, bis[3,3'-di-t-butyl-5,5'-dimethoxy(1,1'-biphenyl)-2,2'-diyl]-2,7,9,9-tetramethyl-9H-xanthin-4,5-diyldiphosphite, compounds represented by the formulae:

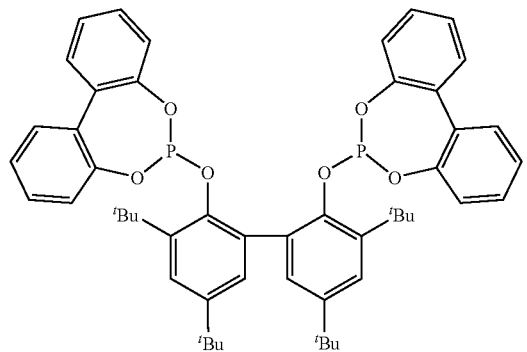

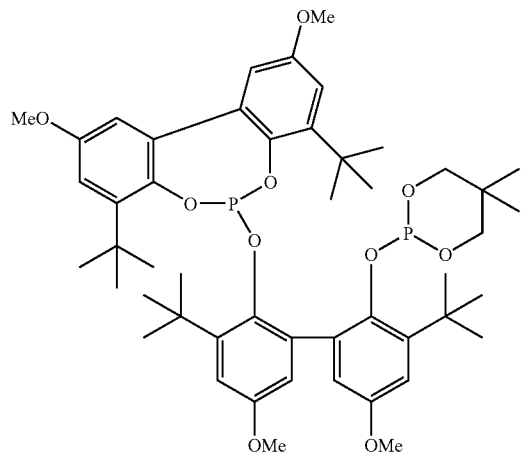

etc. (see, for example, Non-Patent Documents 3 and 4 and Patent Documents 2 and 3); and the like have hitherto been known, and hydroformylation reactions using such a compound have been developed.

Patent Document 1: JP-A-8-10624
Patent Document 2: JP-A-4-290551
Patent Document 3: JP-A-62-116535
Non-Patent Document 1: The Journal of Organic Chemistry, 1969, Vol. 34, No. 2, pages 327 to 330
Non-Patent Document 2: *Journal of the Chemical Society, Chemical Communications,* 1991, pages 1096 to 1097
Non-Patent Document 3: *Organometallics,* 1996, Vol. 15, pages 835 to 847
Non-Patent Document 4: *Helvetica Chimica Acta,* 2001, Vol. 84, pages 3269 to 3280

DISCLOSURE OF THE INVENTION

Problems that the Invention is to Solve

However, though it is known that the hydroformylation reaction using a phosphorus compound as described in the foregoing documents is effective for a hydroformylation reaction of a compound having a carbon-carbon double bond only in a molecular end, such as propylene, 1-octene, etc., results obtained in the case where a non-conjugated diene also having a carbon-carbon double bond in other portion than the molecular end is subjected to a hydroformylation reaction are not described at all. In the hydroformylation reaction, in case of using a non-conjugated diene, there is caused a problem of a lowering of selectivity such as occurrence of undesirable hydroformylation of a carbon-carbon double bond or occurrence of a side reaction such as isomerization of a carbon-carbon double bond, etc. Then, the present inventors applied the foregoing conventional hydroformylation reaction using a rhodium compound and a phosphorus compound to a non-conjugated diene such as 1-methoxy-2,7-octadiene produced through, for example, a telomerization reaction of butadiene in the presence of methanol. As a result, nevertheless the desired product is an aldehyde in which only a carbon-carbon double bond in a molecular end is hydroformylated, there were caused a problem that the hydroformylation reaction to a carbon-carbon double bond in the molecular interior proceeds not a little so that a large quantity of undesirable by-products are formed; and a problem that the isomerization reaction in the carbon-carbon double bond in a molecular end and a molecular interior cannot be suppressed so that a lowering of the yield of the desired aldehyde is unavoidable.

That is, as to a phosphorus compound to be used in a hydroformylation reaction of a non-conjugated diene having a carbon-carbon double bond in an end thereof and having 6 or more carbon atoms, there is room for a further improvement in producing a desired compound.

Thus, an object of the present invention is to provide a bisphosphite which in a hydroformylation reaction of a non-conjugated diene having a carbon-carbon double bond in a molecular end, and especially having from 6 to 20 carbon atoms, is able to simultaneously suppress a hydroformylation reaction to a carbon-carbon double bond in the molecular interior and an isomerization reaction in the respective carbon-carbon double bonds, namely to selectively subject only the carbon-carbon double bond in a molecular end to a hydroformylation reaction and to keep heat stability and resistance to hydrolysis of a catalyst and catalytic activity high; and a method for producing an aldehyde using such a bisphosphite and a group 8 to 10 metal compound.

Means for solving the Problems

According to the present invention, the foregoing object can be achieved by providing:

(1) A method for producing an aldehyde comprising reacting a non-conjugated diene having a carbon-carbon double bond in a molecular end and having from 6 to 20 carbon atoms with a carbon monoxide and hydrogen in the presence of a bisphosphite represented by the general formula (I) [hereinafter referred to as "bisphosphite (I)"]:

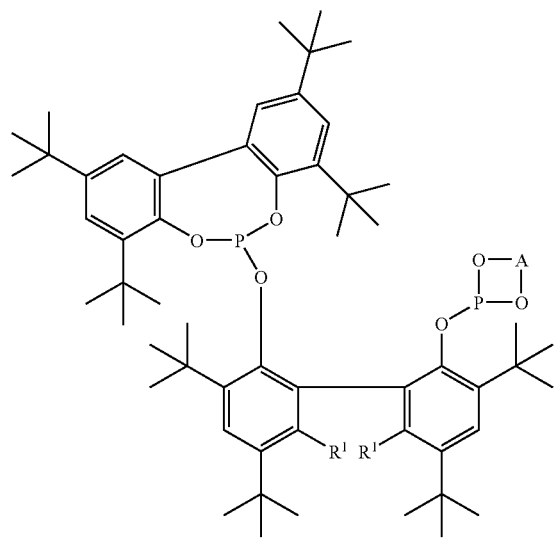

(I)

(in the formula, A represents an alkylene group which may have a substituent, a cycloalkylene group which may have a substituent, a phenylene group which may have a substituent, or a naphthylene group which may have a substituent; and $R^1$ represents a hydrogen atom or an alkyl group) and a group 8 to 10 metal compound;

(2) The method for producing an aldehyde as set forth above in (1), wherein the non-conjugated diene having a carbon-carbon bond double in a molecular end and having from 6 to 20 carbon atoms is 1,4-hexadiene, 1-methoxy-2,7-octadiene, 1-ethoxy-2,7-octadiene, 1-propoxy-2,7-octadiene, 1-isopropoxy-2,7-octadiene, 2,7-octadien-1-ol, 1-acetoxy-2,7-octadiene or 1,6-octadiene; and (3) Such a bisphosphite (I).

ADVANTAGES OF THE INVENTION

According to the present invention, in a hydroformylation reaction of a non-conjugated diene having a carbon-carbon double bond in a molecular end and having from 6 to 20 carbon atoms, it is possible to simultaneously suppress a hydroformylation reaction to a carbon-carbon double bond in the molecular interior and an isomerization reaction in the respective carbon-carbon double bonds, thereby highly selectively obtaining a desired aldehyde. Furthermore, since the bisphosphite (I) of the present invention is extremely high in resistance to hydrolysis and heat stability, the catalytic activity can be kept in the hydroformylation reaction over a long period of time, and industrially stable productivity can be kept. Then, the bisphosphite (I) is useful as ligands for not only the hydroformylation reaction but various reactions using a homogenous noble metal complex catalyst (for example, a hydrogenation reaction, a carbon-carbon bond forming reaction, etc.) or antioxidants of a polymer, etc.

BEST MODES FOR CARRYING OUT THE INVENTION

In the foregoing general formula, examples of the alkylene group represented by A include, an ethylene group, a trimethylene group, a tetramethylene group, a pentamethylene group, groups represented by the following formulae:

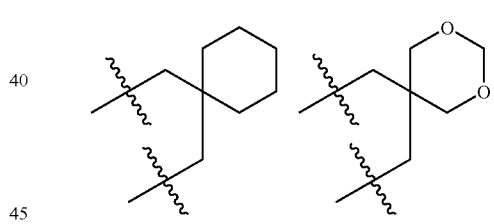

(in the formulae, the wavy line represents a connection site), etc. Examples of the cycloalkylene group represented by A include a cyclopropylene group, a 1,2-cyclopentylene group, a 1,3-cyclopentylene group, 1,2-cyclohexylene group, a 1,3-cyclohexylene group, a 1,4-cyclohexylene group, etc. Examples of the phenylene group represented by A include a 1,2-phenylene group, a 1,3-phenylene group, a 1,4-phenylene group, etc.; and examples of the naphthylene group include a 1,2-naphthylene group, a 1,8-naphthylene group, etc. All of them may have a substituent. Examples of such a substituent include alkyl groups having preferably from 1 to 5 carbon atoms, such as a methyl group, an ethyl group, an n-propyl group, an isopropyl group, an n-butyl group, an isobutyl group, an s-butyl group, a t-butyl group, an n-pentyl group, etc.; alkoxyl groups having preferably from 1 to 4 carbon atoms, such as a methoxy group, an ethoxy group, an n-propoxy group, an isopropoxy group, an n-butoxy group, an isobutoxy group, an s-butoxy group, a t-butoxy group, etc.; aryl groups such as a phenyl group, a naphthyl group, etc.; and the like.

Examples of the alkyl group represented by $R^1$ include alkyl groups having from 1 to 3 carbon atoms, such as a methyl group, an ethyl group, an n-propyl group, an isopropyl group, etc.
Specific examples of the bisphosphite (I) include bisphosphites represented by the following formula:
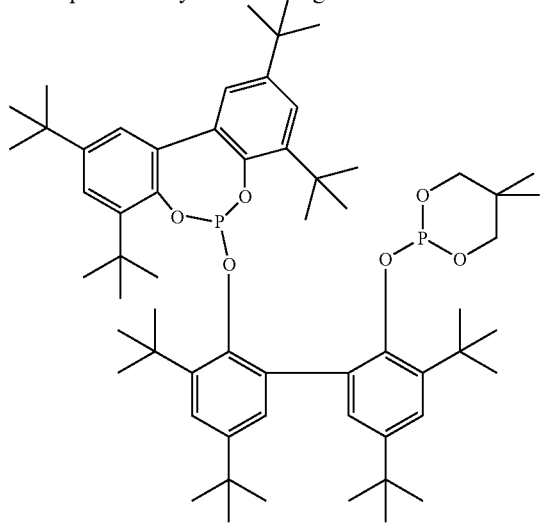
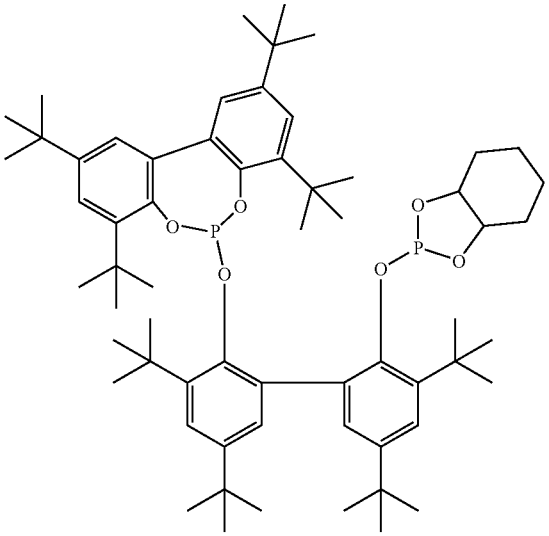
-continued
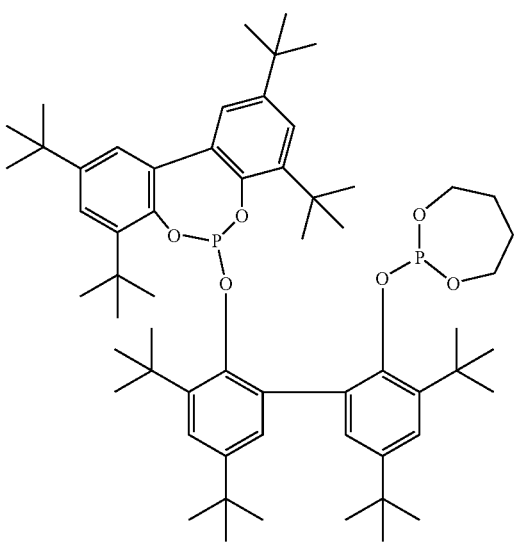

-continued
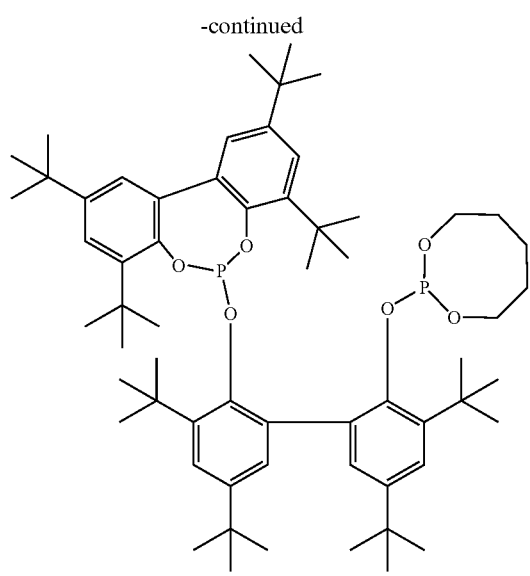
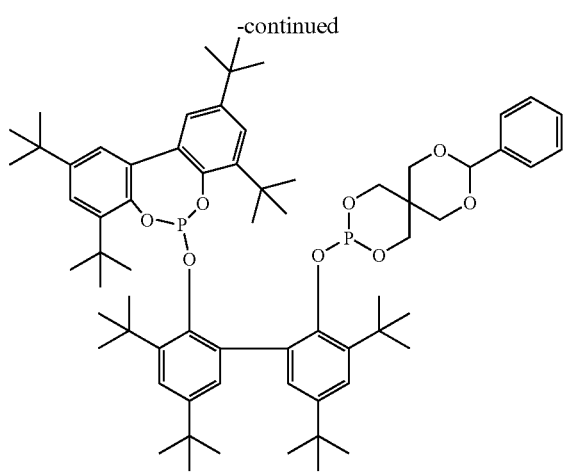
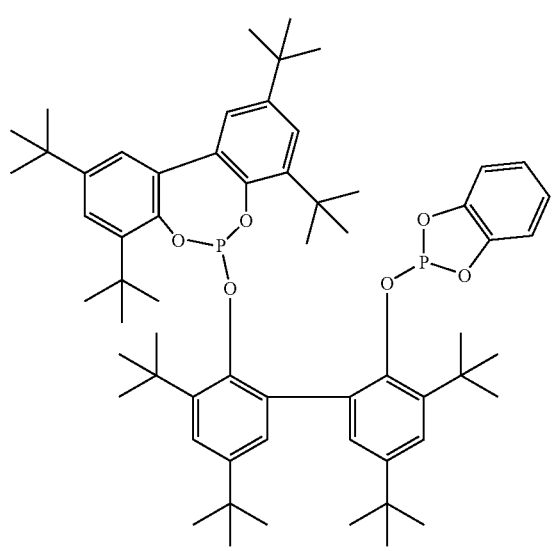
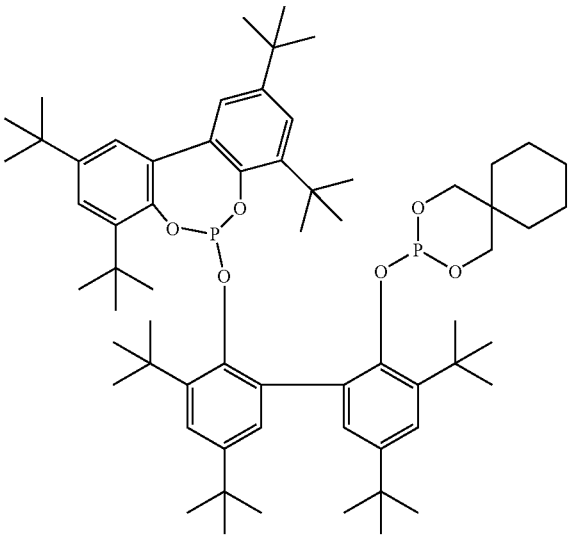
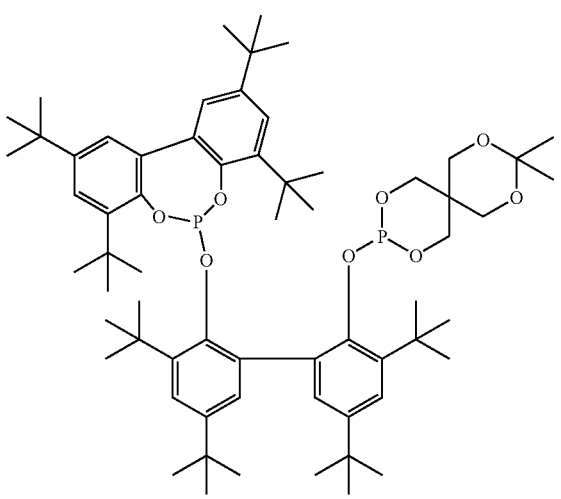
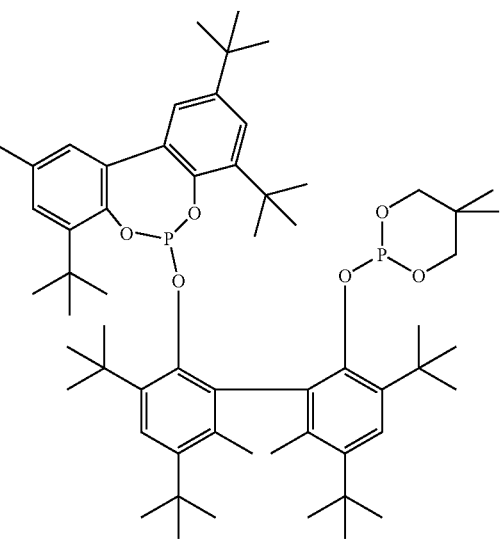

-continued
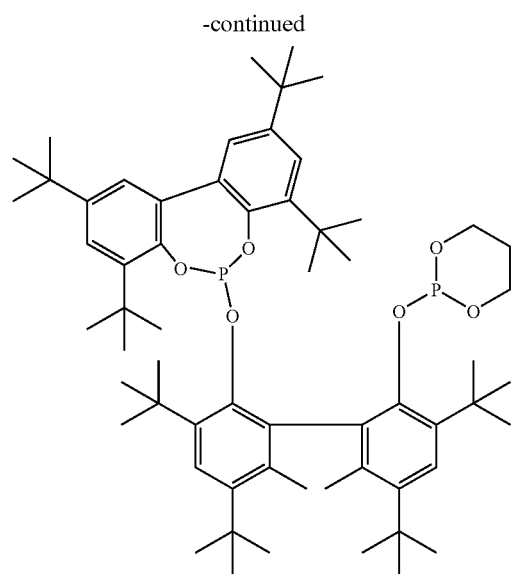
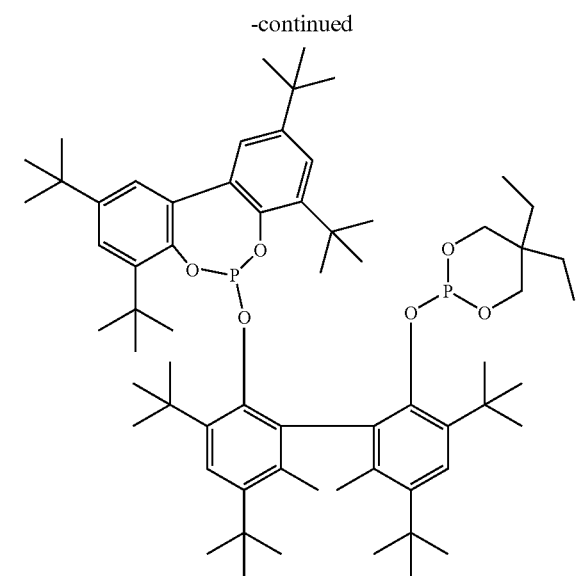
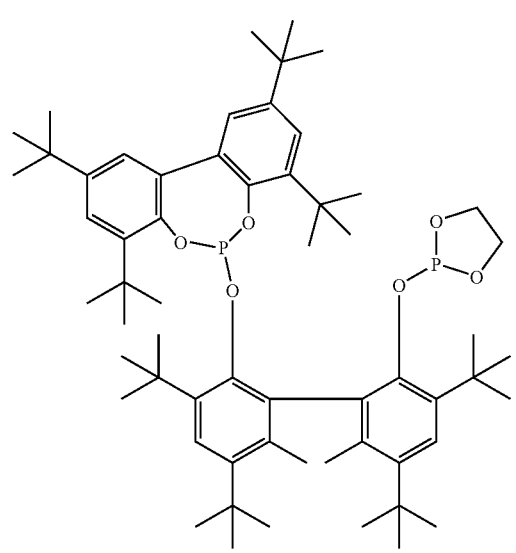
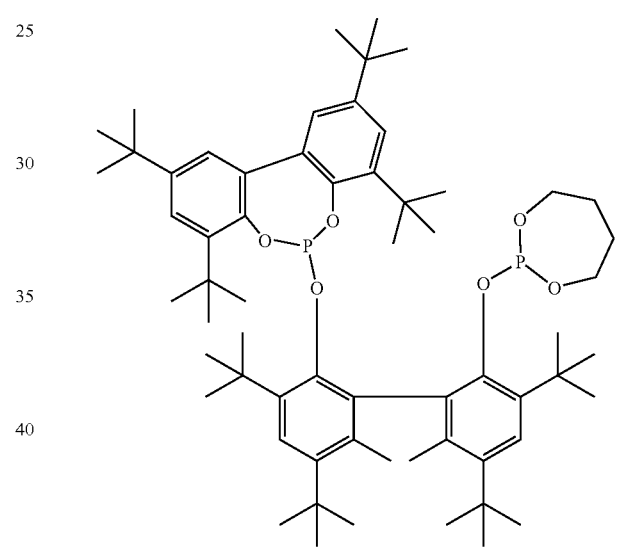
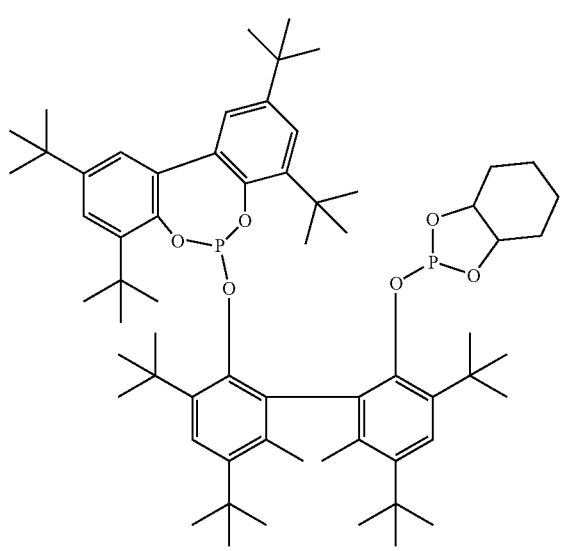
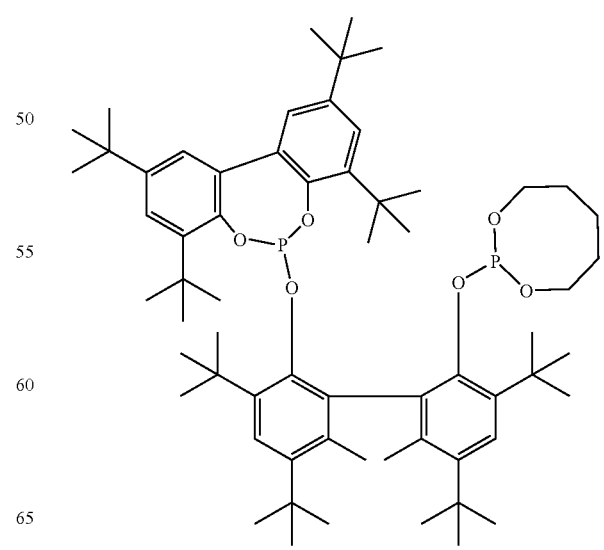

-continued
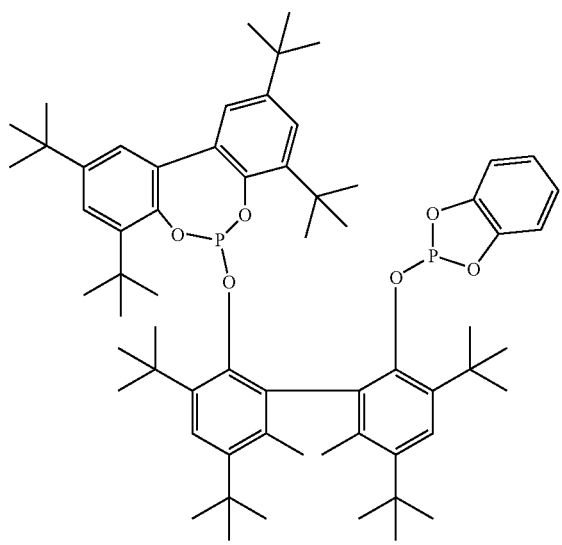
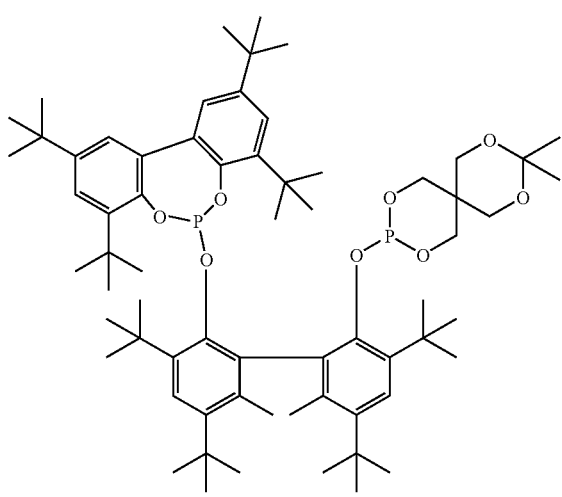
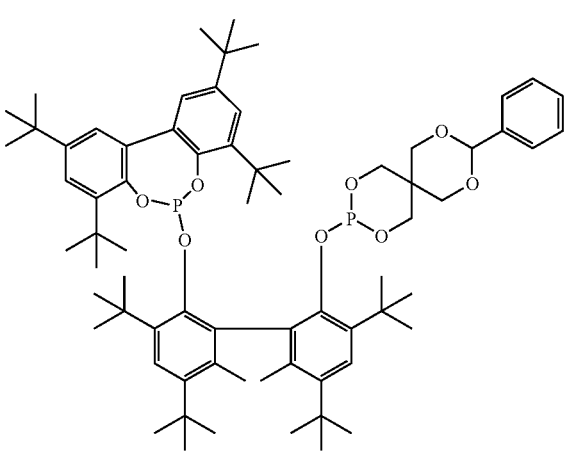
-continued
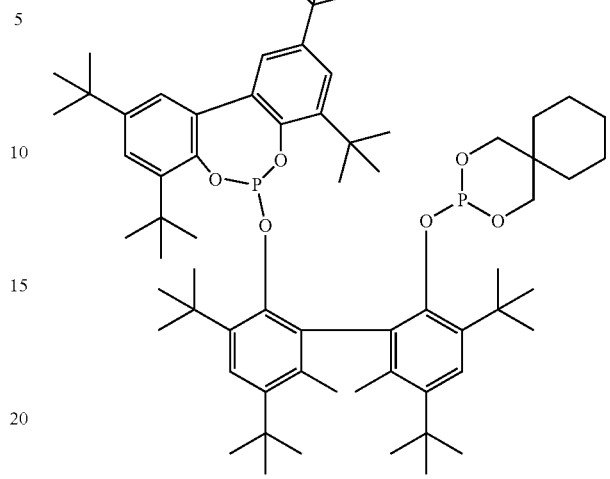
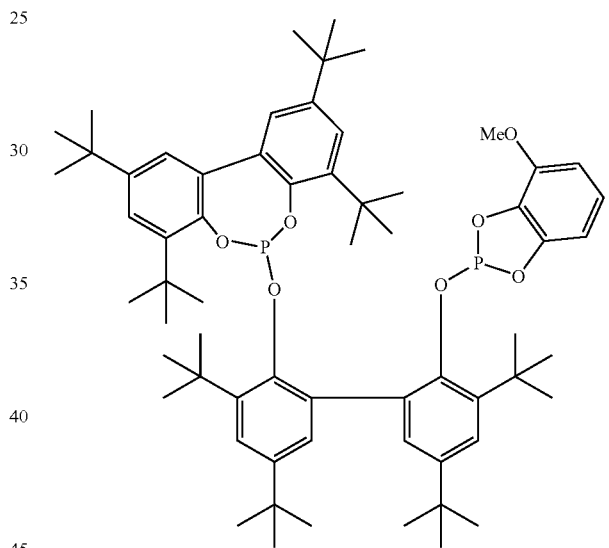
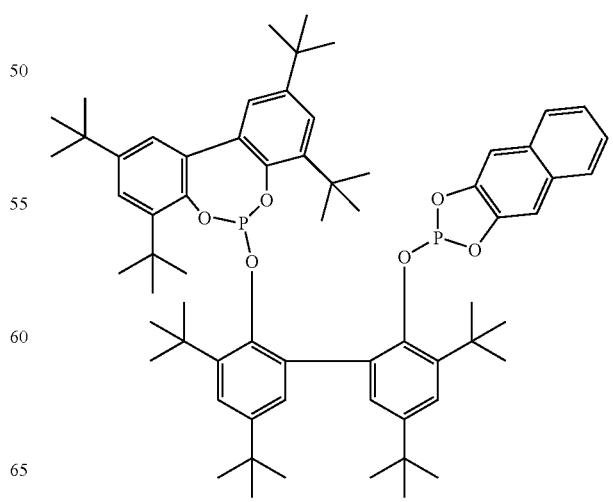

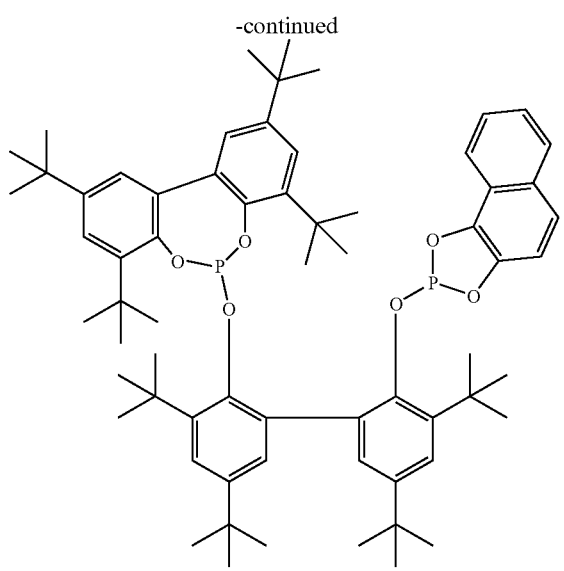

etc.

The production method of the bisphosphite (I) of the present invention is hereunder described.

Though the production method of the bisphosphite (I) is not particularly limited, for example, the following methods are exemplified.

In the case where $R^1$ represents a hydrogen atom, by reacting a bisphenol represented by the formula (A-1) [hereinafter referred to as "bisphenol (A-1)"]:

(A-1)

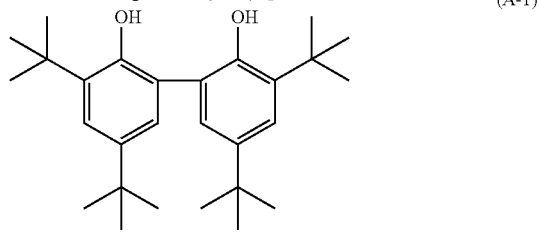

and a phosphorus trihalide compound represented by the general formula: $PY^1{}_3$ ($Y^1$ represents a chlorine atom, a bromine atom or an iodine atom) in an inert gas atmosphere such as nitrogen, argon, etc. in the presence of a solvent and optionally a basic substance, it is possible to produce a monophosphite represented by the formula (C-1) [hereinafter referred to as "monophosphite (C-1)"]

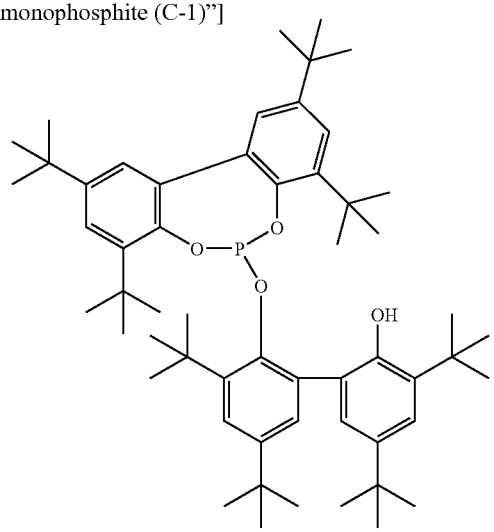

(this method will be hereinafter referred to "monophosphite production method (a)").

On the other hand, in the case where $R^1$ represents an alkyl group, first of all, by reacting a bisphenol represented by the general formula (A-2) [hereinafter referred to as "bisphenol (A-2)"]:

(A-2)

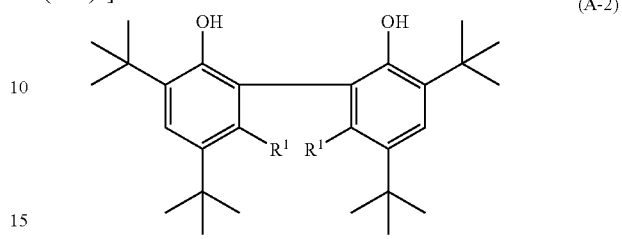

(wherein $R^1$ represents an alkyl group)

and a halogenated phosphite represented by the general formula (B) [hereinafter abbreviated as "halogenated phosphite (B)"]:

(B)

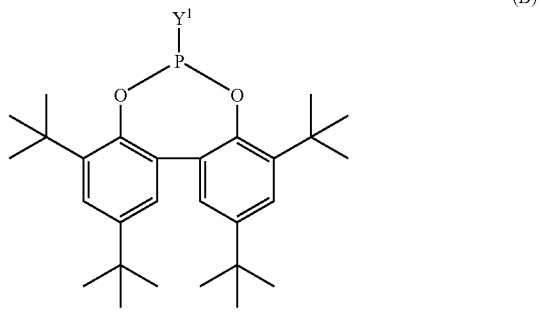

in an inert gas atmosphere such as nitrogen, argon, etc. in the presence of a solvent and optionally a basic substance, it is possible to produce a monophosphite represented by the formula (C-2) [hereinafter referred to as "monophosphite (C-2)"]:

(C-2)

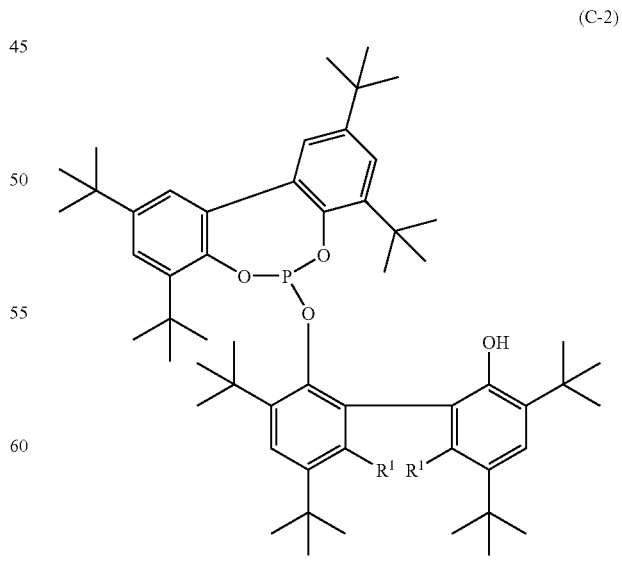

(wherein $R^1$ represents an alkyl group)

(this method will be hereinafter referred to "monophosphite production method (b)").

Subsequently, by [A] reacting the monophosphite (C-1) or monophosphite (C-2) [hereinafter often named generically as "monophosphite (C)"] and a halogenated phosphite represented by the general formula (D) [hereinafter abbreviated as "halogenated phosphite (D)"]:

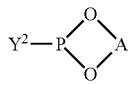
(D)

(in the formula, A is the same as defined above; and $Y^2$ represents a chlorine atom, a bromine atom or an iodine atom) in an inert gas atmosphere such as nitrogen, argon, etc. in the presence of a solvent and optionally a basic substance (this method will be hereinafter referred to as "bisphosphite production method (A)"), or [B] reacting the monophosphite (C) and a phosphorus trihalide compound represented by the general formula: $PY^3_3$ (in the formula, $Y^3$ represents a chlorine atom, a bromine atom or an iodine atom) in an inert gas atmosphere such as nitrogen, argon, etc. in the presence of a solvent and optionally a basic substance to obtain a halogenated phosphite represented by the general formula (E) (hereinafter abbreviated as "halogenated phosphite (E)"):

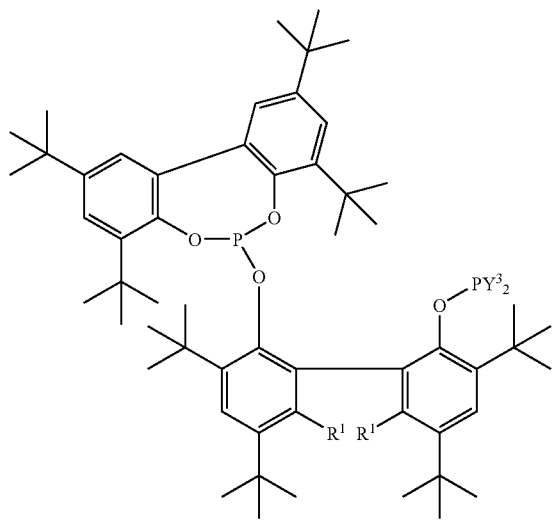
(E)

(this method will be hereinafter referred to as "bisphosphite production method (B-first half)"), and subsequently reacting with a diol represented by the general formula (F) (hereinafter abbreviated as "diol (F)"):

HO-A-OH  (F)

(in the formula, A is the same as defined above)

in an inert gas atmosphere such as nitrogen, argon, etc. in the presence of a solvent and optionally a basic substance (this method will be hereinafter referred to as "bisphosphite production method (B-second half)"), it is possible to produce the bisphosphite (I).

First of all, the monophosphite production method (a) is described in detail.

The use amount of the phosphorus trihalide compound represented by the general formula: $PY^1_3$ (in the formula, $Y^1$ is the same as defined above) is usually in the range of from 0.1 to 1 mole, and preferably in the range of from 0.2 to 0.8 moles per mole of the bisphenol (A-1).

Examples of the basic substance which can be used in the monophosphite production method (a) include amines such as trimethylamine, triethylamine, tri-n-butylamine, tri-n-octylamine, diethylisopropylamine, N,N-dimethylaniline, etc.; nitrogen-containing heterocyclic compounds such as pyridine, picoline, collidine, lutidine, quinoline, etc.; and the like. Of these, it is preferable to use triethylamine or pyridine. The basic substance may be used singly or in combination of two or more thereof.

In the case where the basic substance is used, the use amount of such a basic substance is preferably in the range of from 0.3 to 3 moles per mole of the bisphenol (A-1).

Examples of the solvent which is used in the monophosphite production method (a) include saturated aliphatic hydrocarbons such as pentane, hexane, heptane, octane, nonane, decane, cyclohexane, etc.; aromatic hydrocarbons such as benzene, toluene, ethylbenzene, propylbenzene, o-xylene, m-xylene, p-xylene, o-ethyltoluene, m-ethyltoluene, p-ethyltoluene, etc.; ethers such as dimethyl ether, ethylmethyl ether, diethyl ether, dipropyl ether, butylmethyl ether, t-butylmethyl ether, dibutyl ether, tetrahydrofuran, 1,4-dioxane, etc.; and the like. Of these, it is preferable to use toluene or tetrahydrofuran. The solvent may be used singly or in combination of two or more thereof.

The use amount of such a solvent is preferably in the range of from 1 to 20 parts by mass per part by mass of the bisphenol (A-1).

The conditions in the monophosphite production method (a) such as reaction temperature, reaction pressure, reaction time, etc. are not particularly limited. However, the reaction temperature is usually in the range of from −20 to 100° C., and preferably in the range of from 0 to 50° C. Also, the reaction pressure is usually in the range of from 0.05 to 3 MPa (gauge pressure). In general, the reaction time is preferably in the range of from 1 to 30 hours.

The method for carrying out the monophosphite production method (a) is not particularly limited. For example, the method can be carried out by adding dropwise the phosphorus trihalide compound represented by the general formula: $PY^1_3$ (in the formula, $Y^1$ is the same as defined above) to the bisphenol (A-1) under atmospheric pressure at a prescribed temperature over from one minute to 10 hours in an inert gas atmosphere such as nitrogen, argon, etc. in the presence of a solvent and optionally a basic substance and then reacting the mixture at a prescribed temperature for a prescribed time.

Salts formed as by-products (for example, triethylamine hydrochloride, pyridine hydrochloride, etc.) are removed from the reaction mixture after completion of the reaction as obtained in the foregoing method by means of, for example, filtration, etc., thereby obtaining a mixed solution containing a crude monophosphite (C-1). Such a crude monophosphite (C-1) may be provided for the bisphosphite production method (A) or (B) as described later as it is. Alternatively, it is possible to obtain the monophosphite (C-1) having a higher purity by distilling off the solvent from the mixed solution and subjecting the obtained residue to recrystallization or column chromatography. Such a monophosphite (C-1) may be provided for the bisphosphite production method (A) or (B) as described later.

Next, the monophosphite production method (b) is described in detail.

The use amount of the halogenated phosphite (B) is usually in the range of from 0.8 to 4 moles, and preferably in the range of from 1 to 2 moles per mole of the bisphenol (A-2).

As the basic substance which can be used in the monophosphite production method (b), the same basic substances as those exemplified in the monophosphite production method (a) are exemplified. Of these, it is preferable to use triethylamine or pyridine. The basic substance may be used singly or in combination of two or more thereof.

In the case where the basic substance is used, the use amount of such a basic substance is preferably in the range of from 0.5 to 5 moles per mole of the bisphenol (A-2).

As the solvent to be used in the monophosphite production method (b), the same solvents as those exemplified in the monophosphite production method (a) are exemplified. Of these, it is preferable to use toluene or tetrahydrofuran. The solvent may be used singly or in combination of two or more thereof.

The use amount of such a solvent is preferably in the range of from 1 to 20 parts by mass per part by mass of the bisphenol (A-2).

The conditions in the monophosphite production method (b) such as reaction temperature, reaction pressure, reaction time, etc. are not particularly limited. However, the reaction temperature is usually in the range of from $-20$ to $100°$ C., and preferably in the range of from 0 to $80°$ C. The reaction pressure is usually in the range of from 0.05 to 3 MPa (gauge pressure). In general, the reaction time is preferably in the range of from 0.5 to 20 hours.

The method for carrying out the monophosphite production method (b) is not particularly limited. For example, the method can be carried out by adding dropwise one mole of the halogenated phosphite (B) to one mole of the bisphenol (A-2) under atmospheric pressure at a prescribed temperature over from one minute to 10 hours in an inert gas atmosphere such as nitrogen, argon, etc. in the presence of a solvent and optionally a basic substance and then reacting the mixture at a prescribed temperature for a prescribed time.

Salts formed as by-products (for example, triethylamine hydrochloride, pyridine hydrochloride, etc.) are removed from the reaction mixture after completion of the reaction as obtained in the foregoing method by means of, for example, filtration, etc., thereby obtaining a mixed solution containing a crude monophosphite (C-2). Such a crude monophosphite (C-2) may be provided for the bisphosphite production method (A) or (B) as described later as it is. Alternatively, it is possible to obtain the monophosphite (C-2) having a higher purity by distilling off the solvent from the mixed solution and subjecting the obtained residue to recrystallization or column chromatography. Such a monophosphite (C-2) may be provided for the bisphosphite production method (A) or (B) as described later.

The halogenated phosphite (B) to be used in the monophosphite production method (b) can be produced by, for example, by reacting one mole of the phosphorus trihalide compound such as phosphorus trichloride, etc. and one mole of the bisphenol (A-1) at about $-10°$ C. under atmospheric pressure in an inert gas atmosphere such as nitrogen, argon, etc. optionally in the presence of a basic substance such as triethylamine, etc. and a solvent such as toluene, etc. (see, for example, *Journal of Chemical Society*, 1953, pages 1920 to 1926), and furthermore, the purity can be properly increased by distillation or recrystallization.

Next, the bisphosphite production method (A) is described in detail.

In the bisphosphite production method (A), the use amount of the halogenated phosphite (D) is preferably in the range of from 0.8 to 3 moles, and more preferably in the range of from 1 to 2 moles per mole of the monophosphite (C).

As the basic substance which can be used in the bisphosphite production method (A), in addition to the basic substances exemplified in the monophosphite production method (a), metal hydrides such as sodium hydride, potassium hydride, etc.; alkyllithiums such as methyllithium, n-butyllithium, etc.; and the like are exemplified. Of these, it is preferable to use triethylamine, pyridine, n-butyllithium or sodium hydride. The basic substance may be used singly or in combination of two or more thereof. In the case where the basic substance is used, the use amount of such a basic substance is preferably in the range of from 0.8 to 2 moles per mole of the monophosphite (C).

As the solvent, the same solvents as those exemplified in the monophosphite production method (a) are exemplified. Of these, it is preferable to use toluene or tetrahydrofuran. The solvent may be used singly or in combination of two or more thereof.

The use amount of such a solvent is preferably in the range of from 1 to 100 parts by mass per part by mass of the monophosphite (C).

The conditions in the bisphosphite production method (A) such as reaction temperature, reaction pressure, reaction time, etc. are not particularly limited. However, the reaction temperature is usually in the range of from $-100$ to $100°$ C., and preferably in the range of from $-80$ to $80°$ C. The reaction pressure is usually in the range of from 0.05 to 3 MPa (gauge pressure). In general, the reaction time is preferably in the range of from 0.5 to 30 hours.

The method for carrying out the bisphosphite production method (A) is not particularly limited. For example, the method can be carried out by adding dropwise the halogenated phosphite (D) to the monophosphite (C) under atmospheric pressure at a prescribed temperature over from one minute to 10 hours in an inert gas atmosphere such as nitrogen, argon, etc. in the presence of a solvent and optionally a basic substance and then reacting the mixture at a prescribed temperature for a prescribed time. In particular, in the case where the foregoing metal hydride or alkyllithium is used as the basic substance, in general, the method can be carried out by previously reacting the monophosphite (C) with the metal hydride or alkyllithium to convert it into a phenoxide, to which is then added dropwise the halogenated phosphite (D) at a prescribed temperature over from one minute to 10 hours, and reacting the mixture at a prescribed temperature for a prescribed time.

Salts formed as by-products (for example, triethylamine hydrochloride, pyridine hydrochloride, etc.) are removed from the reaction mixture after completion of the reaction as obtained in the foregoing method by means of, for example, filtration, etc.; the solvent is then distilled off from the reaction mixture; and the obtained residue is subjected to recrystallization, whereby the bisphosphite (I) having a higher purity can be obtained.

The halogenated phosphite (D) to be used in the bisphosphite production method (A) can be produced by, for example, by reacting a phosphorus trihalide compound such as phosphorus trichloride, etc. and the diol (F) to be used in the bisphosphite production method (B) as described later at about $-10°$ C. under atmospheric pressure in an inert gas atmosphere such as nitrogen, argon, etc. optionally in the presence of a basic substance such as triethylamine, etc. and a solvent such as tetrahydrofuran, toluene, etc. (see, for example, *Journal of Chemical Society*, 1953, pages 1920 to 1926), and furthermore, the purity can be properly increased by a usual separation and purification method of an organic compound such as distillation, recrystallization, etc.

The bisphosphite production method (B-first half) is hereunder described in detail.

The use amount of the phosphorus trihalide compound represented by the general formula: $PY^3{}_3$ (in the formula, $Y^3$ is the same as defined above) is usually in the range of from 1 to 100 moles, and preferably in the range of from 1 to 10 mole per mole of the monophosphite (C).

As the basic substance which can be used in the bisphosphite production method (B-first half), the same basic substances as those used in the monophosphite production method (a) are exemplified. Of these, it is preferable to use triethylamine or pyridine. The basic substance may be used singly or in combination of two or more thereof.

In the case where the basic substance is used, its use amount is preferably in the range of from 1 to 10 moles per mole of the monophosphite (C).

As the solvent to be used in the bisphosphite production method (B-first half), the same solvents as those used in the monophosphite production method (a) are exemplified. Of these, it is preferable to use toluene or tetrahydrofuran. The solvent may be used singly or in combination of two or more thereof.

The use amount of such a solvent is preferably in the range of from 1 to 100 parts by mass per part by mass of the monophosphite (C).

The conditions in the bisphosphite production method (B-first half) such as reaction temperature, reaction pressure, reaction time, etc. are not particularly limited. However, the reaction temperature is usually in the range of from 0 to 150° C., and preferably in the range of from 20 to 120° C. Also, the reaction pressure is usually in the range of from 0.05 to 3 MPa (gauge pressure). In general, the reaction time is preferably in the range of from 0.5 to 30 hours.

The method for carrying out the bisphosphite production method (B-first half) is not particularly limited. For example, the method can be carried out by adding dropwise the phosphorus trihalide compound represented by the general formula: $PY^3_3$ (in the formula, $Y^3$ is the same as defined above) to the monophosphite (C) under atmospheric pressure at a prescribed temperature over from one minute to 10 hours in an inert gas atmosphere such as nitrogen, argon, etc. in the presence of a solvent and optionally a basic substance and then reacting the mixture at a prescribed temperature for a prescribed time.

The residue containing the halogenated phosphite (E) which is obtained by filtering the reaction mixture containing the halogenated phosphite (E) obtained by the foregoing method and distilling off the foregoing phosphorus trihalide compound, solvent, basic substance, etc. under a reduced pressure (at 50° C. and 0.01 MPa) may be used for the bisphosphite production method (B-second half) as described later as it is. Alternatively, the halogenated phosphite (E) is isolated by recrystallization from a solvent such as toluene, tetrahydrofuran, etc. and then used for the bisphosphite production method (B-second half).

Next, the bisphosphite production method (B-second half) is hereunder described in detail.

The use amount of the diol (F) to be used in the bisphosphite production method (B-second half) is usually in the range of from 1 to 10 moles, and preferably in the range of from 1 to 3 mole per mole of the halogenated phosphite (E).

As the basic substance which can be used in the bisphosphite production method (B-second half), the same basic substances as those used in the monophosphite production method (a) are exemplified. Of these, it is preferable to use triethylamine or pyridine. The basic substance may be used singly or in combination of two or more thereof.

In the case where the basic substance is used, its use amount is preferably in the range of from 2 to 10 moles per mole of the halogenated phosphite (E).

As the solvent to be used in the bisphosphite production method (B-second half), the same solvents as those exemplified in the monophosphite production method (a) are exemplified. Of these, it is preferable to use toluene or tetrahydrofuran. The solvent may be used singly or in combination of two or more thereof.

The use amount of such a solvent is preferably in the range of from 1 to 100 parts by mass per part by mass of the halogenated phosphite (E).

The conditions in the bisphosphite production method (B-second half) such as reaction temperature, reaction pressure, reaction time, etc. are not particularly limited. However, the reaction temperature is usually in the range of from −20 to 100° C., and preferably in the range of from 0 to 50° C. Also, the reaction pressure is usually in the range of from 0.05 to 3 MPa (gauge pressure). In general, the reaction time is preferably in the range of from 0.5 to 30 hours.

The method for carrying out the bisphosphite production method (B-second half) is not particularly limited. For example, the method can be carried out by adding dropwise the diol (F) to the halogenated phosphite (E) obtained in the bisphosphite production method (B-first half) under atmospheric pressure at a prescribed temperature over from one minute to 10 hours in an inert gas atmosphere such as nitrogen, argon, etc. in the presence of a solvent and optionally a basic substance and then reacting the mixture at a prescribed temperature for a prescribed time.

As to the separation and purification of the bisphosphite (I) from the reaction mixture obtained by the foregoing method, the bisphosphite (I) having a high purity can be obtained by, for example, removing salts formed as by-products (for example, triethylamine hydrochloride, pyridine hydrochloride, etc.) by means of filtration, etc., distilling off the solvent from the reaction mixture and then subjecting the obtained crude product to recrystallization. The recrystallization can be carried out by, for example, dissolving the crude product in a solvent such as hexane, toluene, diisopropyl ether, tetrahydrofuran, ethyl acetate, acetone, acetonitrile, etc. upon heating at a temperature in the range of from 40° C. to a boiling point of the solvent and cooling to from −20 to 20° C., followed by allowing to stand.

The bisphosphite (I) obtained by the foregoing method is a novel compound. Such a bisphosphite (I) has such a characteristic not seen in the conventionally known bisphosphites that in a hydroformylation reaction of a non-conjugated diene having a carbon-carbon double bond in a molecular end, and especially having from 6 to 20 carbon atoms, it is able to simultaneously suppress a hydroformylation reaction to a carbon-carbon double bond in the molecular interior and an isomerization reaction in the respective carbon-carbon double bonds and to keep heat stability and catalytic activity high, and is very useful.

A method for producing an aldehyde through a reaction (hydroformylation reaction) of a non-conjugated diene having a carbon-carbon double bond in a molecular end and having from 6 to 20 carbon atoms with carbon monoxide and hydrogen in the presence of the bisphosphite (I) and a group 8 to 10 metal compound (this method will be hereinafter referred to as "reaction 1") is hereunder described in detail.

Specific examples of the non-conjugated diene having a carbon-carbon double bond in a molecular end and having from 6 to 20 carbon atoms include 1,4-hexadiene, 1-methoxy-2,7-octadiene, 1-ethoxy-2,7-octadiene, 1-propoxy-2,7-octadiene, 1-isopropoxy-2,7-octadiene, 2,7-octadien-1-ol, 1-acetoxy-2,7-octadiene, 1,6-octadiene, etc.

Examples of the group 8 to 10 metal compound include rhodium compounds, cobalt compounds, ruthenium compounds, iron compounds, etc. Examples of the rhodium compound include $Rh(acac)(CO)_2$, $Rh(acac)_3$, $RhCl(CO)(PPh_3)_2$, $RhCl(PPh_3)_3$, $RhBr(CO)(PPh_3)_2$, $Rh_4(CO)_{12}$, $Rh_6(CO)_{16}$, etc. Examples of the cobalt compound include $HCo(CO)_3$, $HCo(CO)_4$, $Co_2(CO)_8$, $HCo_3(CO)_9$, etc. Examples of the ruthenium compound include $Ru(CO)_3(PPh_3)_2$, $RuCl_2$ (PPh$_3$)$_3$, RuCl$_3$(PPh$_3$)$_3$, Ru$_3$(CO)$_{12}$, etc. Also, examples of the iron compound include Fe(CO)$_5$, Fe(CO)$_4$PPh$_3$, Fe(CO)$_4$(PPh$_3$)$_2$, etc. Of these, it is preferable to use a rhodium compound which is easy to select a relatively mild reaction condition; and it is especially preferable from the viewpoint of easiness of availability to use Rh(acac) (CO)$_2$ or Rh(acac)$_3$.

The use amount of the group 8 to 10 metal compound is preferably in the range of from 0.0001 to 1,000 moles, and more preferably in the range of from 0.005 to 10 moles as reduced into a metal atom per liter of the reaction mixture. When the use amount of the group 8 to 10 metal compound is less than 0.0001 moles per liter of the reaction mixture, the reaction rate tends to become extremely slow; and also, even when it exceeds 1,000 moles, an effect corresponding thereto is not obtained, but the catalyst costs merely increase.

In the reaction 1, the bisphosphite (I) may be used singly or in combination of two or more thereof. The use amount of such a bisphosphite (I) is preferably in the range of from 2 to 1,000 moles, and more preferably in the range of from 5 to 500 moles as reduced into a phosphorus atom per mole of the metal in the group 8 to 10 metal compound, with a range of from 10 to 200 moles being further preferable from the viewpoints of catalytic activity and reaction rate. In the case where the use amount of the bisphosphite (I) is less than 2 moles per mole of the metal in the group 8 to 10 metal compound, the heat stability of the catalyst is impaired; and also, in the case where it exceeds 1,000 moles, the reaction rate tends to become extremely small.

The reaction 1 is carried out in the presence or absence of a solvent. Examples of such a solvent include saturated aliphatic hydrocarbons such as pentane, hexane, heptane, octane, nonane, decane, cyclohexane, etc.; aromatic hydrocarbons such as benzene, toluene, ethylbenzene, propylbenzene, o-xylene, m-xylene, p-xylene, o-ethyltoluene, m-ethyltoluene, p-ethyltoluene, etc.; alcohols such as isopropyl alcohol, isobutyl alcohol, isopentyl alcohol, neopentyl alcohol, etc.; ethers such as dimethyl ether, ethylmethyl ether, diethyl ether, dipropyl ether, butylmethyl ether, t-butylmethyl ether, dibutyl ether, ethylphenyl ether, diphenyl ether, tetrahydrofuran, 1,4-dioxane, etc.; ketones such as acetone, ethyl methyl ketone, methyl propyl ketone, diethyl ketone, ethyl propyl ketone, dipropyl ketone, etc.; and the like. Such a solvent may be used singly or in combination of two or more thereof. In the case where the solvent is used, though the use amount of the solvent is not particularly limited, in general, it is preferably in the range of from 1 to 90% by mass relative to the whole of the reaction mixture.

The reaction temperature in the reaction 1 is preferably in the range of from 40 to 150° C.; and from the viewpoint of suppressing deactivation of the catalyst, it is more preferably in the range of from 50 to 130° C. Also, the reaction pressure is preferably in the range of from 0.01 to 10 MPa (gauge pressure), and more preferably in the range of from 0.5 to 5 MPa (gauge pressure).

The reaction time is usually in the range of from 0.5 to 20 hours; and from the viewpoint of productivity, it is preferably in the range of from 0.5 to 5 hours.

As to the use proportion of a mixed gas of carbon monoxide and hydrogen to be used in the reaction 1, a ratio of carbon monoxide to hydrogen is preferably in the range of from 10/1 to 1/10 (by mole), and more preferably in the range of from to 1/2 (by mole).

For the purpose of suppressing the occurrence of high boiling of the formed aldehyde due to a side reaction, if desired, the reaction 1 may be carried out in the presence of an additive such as triethylamine, tributylamine, tri-n-octylamine, N,N,N',N'-tetramethyl-1,2-diaminoethane, N,N,N',N'-tetramethyl-1,3-diaminopropane, N,N,N',N'-tetramethyl-1,4-diaminobutane, N,N-diethylethanolamine, triethanolamine, N-methylpiperidine, N-methylpyrrolidine, N-methylmorpholine, pyridine, picoline, lutidine, collidine, quinoline, etc. In the case where the additive is used, in general, its use amount is preferably in the range of from 200 to 3,000 moles, and more preferably in the range of from 800 to 2,000 moles per mole of the metal in the group 8 to 10 metal compound.

The reaction 1 can be carried out in a continuous manner or a batchwise manner by using a stirring type reaction tank, a circulation type reaction tank, a bubble tower type reaction tank, etc.

The method for carrying out the reaction 1 is not particularly limited. For example, the method can be carried out by charging the non-conjugated diene having a carbon-carbon double bond in a molecular end and having from to 20 carbon atoms in the presence of a mixed gas of carbon monoxide and hydrogen in a molar ratio of 1/1 and feeding a mixed solution of the bisphosphite (I), the group 8 to 10 metal compound and the solvent and optionally the foregoing additive while stirring and reacting the mixture at a prescribed temperature and a prescribed pressure for a prescribed time.

Though the separation and purification method of an aldehyde from the reaction mixture obtained in the foregoing method is not particularly limited, it can be carried out by a method which is used for usual separation and purification of an organic compound. For example, an aldehyde having a high purity can be obtained by distilling off the solvent, the basic substance, etc. from the reaction mixture under a reduced pressure (at 50° C./0.01 MPa) and then distilling the residue under a reduced pressure. Also, prior to such distillation, the bisphosphite (I) and the group 8 to 10 metal compound may be separated by subjecting the residue to a method such as vaporization, extraction, adsorption, etc. The separated bisphosphite (I) and the group 8 to 10 metal compound can be again used for the hydroformylation reaction (reaction 1).

EXAMPLES

The present invention is hereunder described in more detail with reference to the Examples, but it should be construed that the present invention is never limited to these Examples.

Example 1

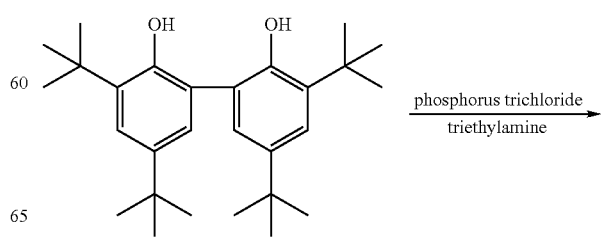

-continued

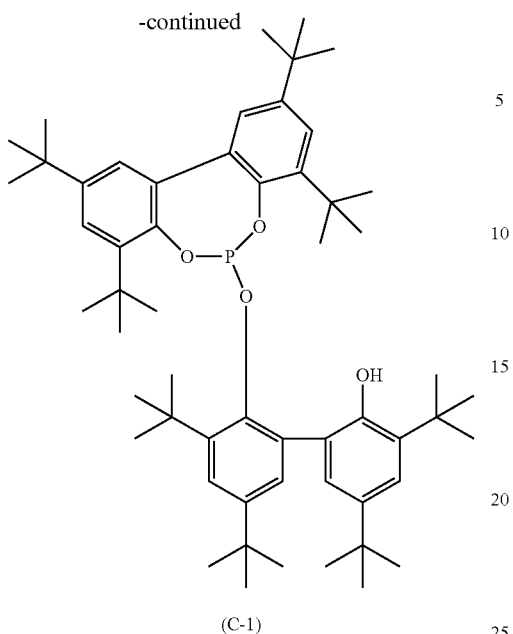

(C-1)

In a three-necked flask equipped with a thermometer and a dropping funnel and having an inner volume of 1,000 mL, 82.12 g (200 mmoles) of 4,4',6,6'-tetra-tert-butyl-2,2'-biphenol and 500 mL of toluene were added, and 59.2 g (390 mmoles) of triethylamine was further added, followed by substituting the inside of the system with nitrogen. Subsequently, 11.4 mL (130 mmoles) of phosphorus trichloride was added dropwise over 30 minutes so as to keep the inner temperature at 20 to 30° C., and after completion of the dropwise addition, the mixture was further stirred at room temperature for 12 hours. After completion of the reaction, triethylamine hydrochloride formed as a by-product was removed by means of filtration, and the toluene and triethylamine were distilled off from the obtained filtrate under a reduced pressure (at 50° C./0.01 MPa), thereby obtaining 95.0 g of a crude monophosphite (C-1). This was purified by recrystallization from a mixed solvent of 300 mL of acetonitrile and 150 mL of tetrahydrofuran, thereby obtaining 82.80 g of the monophosphite (C-1) (yield on the basis of phosphorus trichloride: 75%, purity: 99%).

Example 2

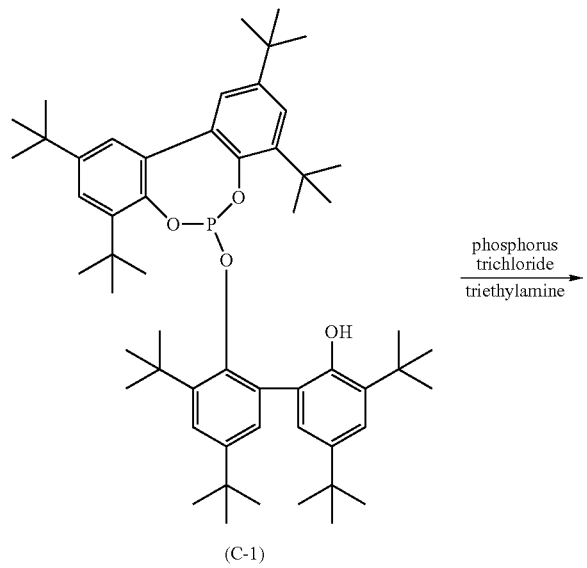

(C-1)

-continued

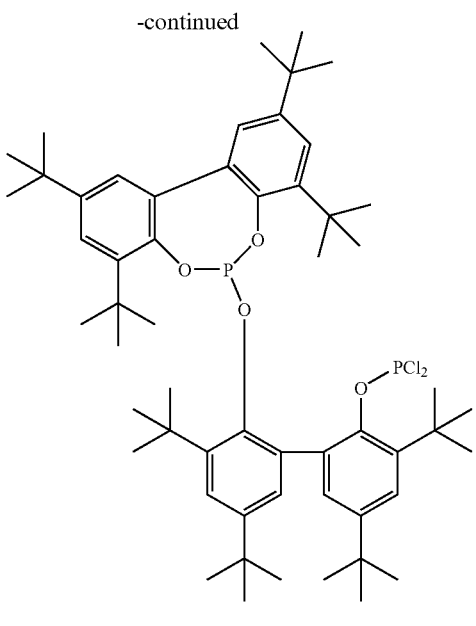

(E-1)

In a three-necked flask equipped with a thermometer and a dropping funnel and having an inner volume of 100 mL, 8.49 g (10 mmoles) of the monophosphite (C-1) and 50 mL of toluene were added, and 1.52 mg (15 mmoles) of triethylamine was further added, followed by substituting the inside of the system with nitrogen. Subsequently, 2.6 mL (30 mmoles) of phosphorus trichloride was added dropwise over 30 minutes so as to keep the inner temperature at 20 to 30° C. After completion of the dropwise addition, the temperature was raised to 70° C., and the mixture was further stirred for 12 hours. After returning to room temperature, triethylamine hydrochloride formed as a by-product was removed by means of filtration, and the phosphorus trichloride, toluene and triethylamine were distilled off from the obtained filtrate under a reduced pressure (at 50° C./0.01 MPa), thereby obtaining 10.5 g of a crude halogenated phosphite (E-1).

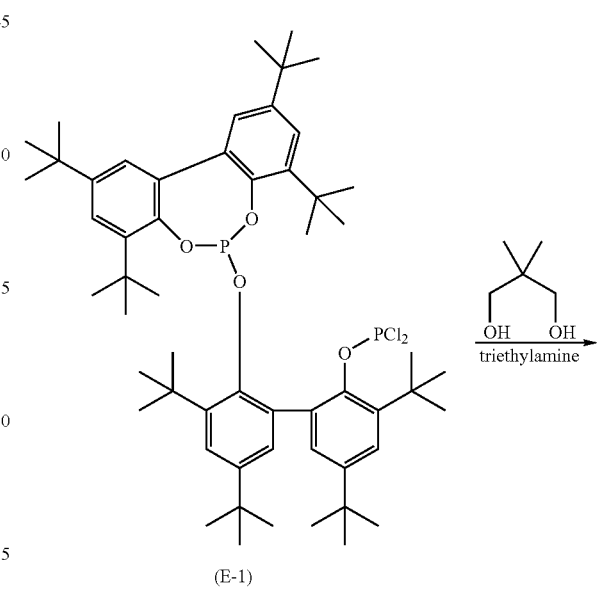

(E-1)

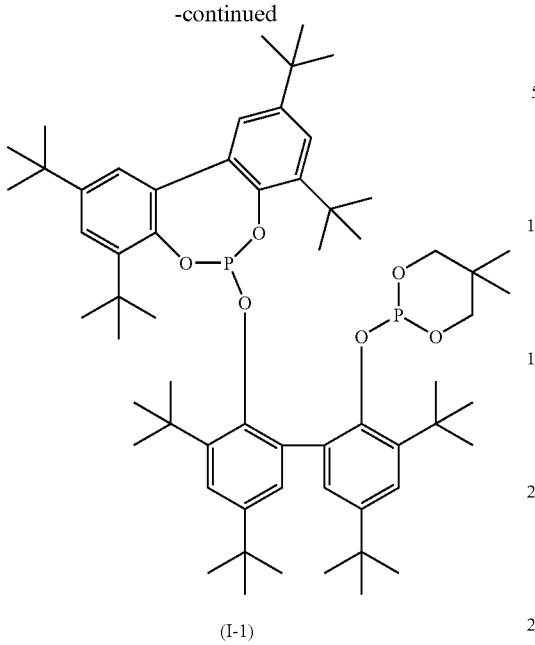

(I-1)

Subsequently, in a three-necked flask equipped with a thermometer and a dropping funnel and having an inner volume of 300 mL, 10.5 g of the above-obtained crude halogenated phosphite (E-1), 100 mL of toluene and 3.03 g (30 mmoles) of triethylamine were added, followed by substituting the inside of the system with nitrogen. Subsequently, a solution of 1.56 g (15 mmoles) of neopentyl glycol dissolved in 10 mL of tetrahydrofuran was added dropwise over 30 minutes so as to keep the inner temperature at 20 to 30° C. After completion of the dropwise addition, the mixture was further stirred at room temperature for 3 hours; thereafter, triethylamine hydrochloride formed as a by-product was removed by means of filtration; and the toluene, tetrahydrofuran and triethylamine were distilled off from the obtained filtrate under a reduced pressure (at 50° C./0.01 MPa), thereby obtaining 10.9 g of a crude bisphosphite (I-1). 50 mL of acetonitrile was added thereto, and the mixture was stirred at room temperature for 30 minutes, followed by filtration to obtain a solid. 80 mL of diisopropyl ether was added thereto, and the mixture was heated at 70° C. After confirming that the solid had been entirely dissolved, this solution was cooled to 5° C. over one hour, and a deposited crystal was collected by filtration. This was dried at room temperature under a reduced pressure, thereby obtaining 6.73 g of the bisphosphite (I-1) (yield on the basis of the monophosphite (C-1): 68%, purity: 98%). An $^1$H-NMR data of the obtained bisphosphite (I-1) is shown below.

$^1$H-NMR (270 MHz, CDCl$_3$, TMS) δ: 7.40 to 7.06 (m, 8H), 4.14 (dd, 1H, J=3.0, 10.8 Hz), 3.88 (dd, 1H, J=3.0, 10.8 Hz), 3.29 (dt, 1H, J=3.0, 10.8 Hz), 2.90 (dt, 1H, J=3.0, 10.8 Hz), 1.48 (s, 9H), 1.45 (s, 9H), 1.33 (s, 9H), 1.31 (s, 9H), 1.29 (s, 9H), 1.27 (s, 9H), 1.22 (s, 9H), 1.01 (s, 6H)

Example 3

The reaction and separation and purification operation were carried out in the same manner as in Example 2, except that in Example 2, 1.35 g (15 mmoles) of 1,4-butanediol was used in place of 1.56 g (15 mmoles) of neopentyl glycol, thereby obtaining 6.96 g of a bisphosphite (I-2) (yield on the basis of the monophosphite (C-1): 72%, purity: 98%) represented by the formula (I-2).

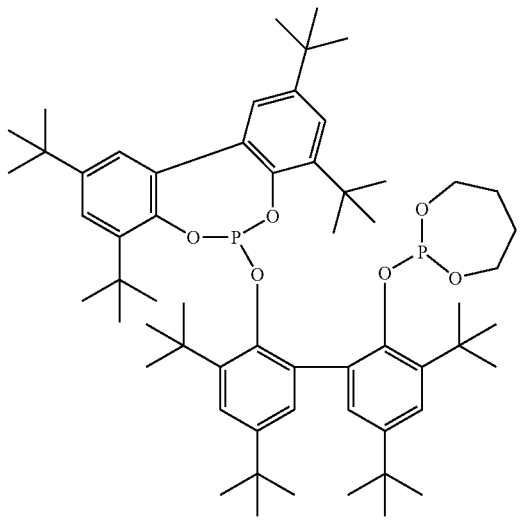

(I-2)

An $^1$H-NMR data of the obtained bisphosphite (I-2) is shown below.

$^1$H-NMR (270 MHz, CDCl$_3$, TMS) δ: 7.39 to 7.04 (m, 8H), 4.27 to 4.15 (m, 1H), 3.77 to 3.65 (m, 1H), 3.62 to 3.48 (m, 1H), to 3.18 (m, 1H), 1.48 (s, 9H), 1.45 (s, 9H), 1.33 to 1.28 (m, 58H)

Example 4

The reaction and separation and purification operation were carried out in the same manner as in Example 2, except that in Example 2, 0.93 g (15 mmoles) of ethylene glycol was used in place of 1.56 g (15 mmoles) of neopentyl glycol, thereby obtaining 6.57 g of a bisphosphite (I-3) (yield on the basis of the monophosphite (C-1): 70%, purity: 96%) represented by the formula (I-3).

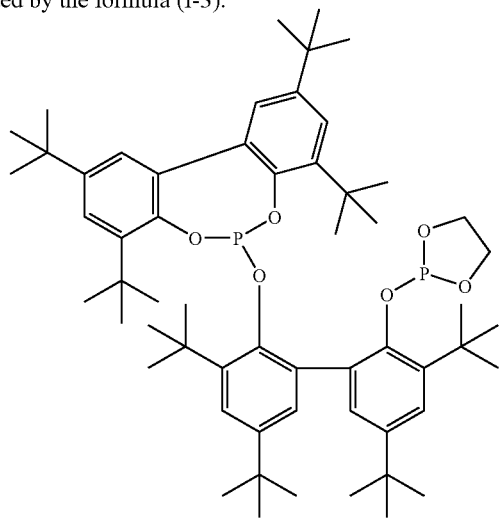

An $^1$H-NMR data of the obtained bisphosphite (I-3) is shown below.

$^1$H-NMR (270 MHz, CDCl$_3$, TMS) δ: 7.41 to 7.05 (m, 8H), 4.18 to 4.14 (m, 1H), 4.11 to 4.02 (m, 1H), 3.91 to 3.85 (m, 1H) to 3.69 (m, 1H), 1.44 (s, 9H), 1.40 (s, 9H), 1.33 (s, 9H) (s, 9H), 1.29 (s, 9H), 1.27 (s, 9H), 1.20 (s, 9H), 1.05 (s, 9H)

Example 5

In a three-necked flask equipped with a thermometer and a dropping funnel and having an inner volume of 100 mL, 8.49 g (10 mmoles) of the monophosphite (C-1) obtained in Example 1 and 50 mL of tetrahydrofuran were added, followed by substituting the inside of the system with nitrogen. After cooling the inside of the system to −70° C., 6.3 mL of a hexane solution of 1.6 moles/L of n-butyllithium (corresponding to 10 mmoles of n-butyllithium) was added dropwise over one hour so as to keep the inner temperature at not higher than −60° C. After completion of the dropwise addition, the mixture was further stirred at −70° C. for 30 minutes. To the obtained reaction mixture, 2.09 g (12 mmoles) of 1,2-phenylene phosphorochloridite was added dropwise over 30 minutes so as to keep the inner temperature at not higher than −60° C. After completion of the dropwise addition, the mixture was further stirred at the same temperature for 2 hours, and thereafter, the temperature was gradually raised to 0° C. Lithium chloride formed as a by-product was removed from the reaction mixture by filtration, and the filtrate was concentrated under a reduced pressure (at 50° C./0.01 MPa), thereby obtaining 24.01 g of a residue. This residue was recrystallized from 100 mL of diisopropyl ether, thereby 8.10 g of a bisphosphite (I-4) (yield on the basis of the monophosphite (C-1): 82%, purity: 98%) represented by the formula (I-4).

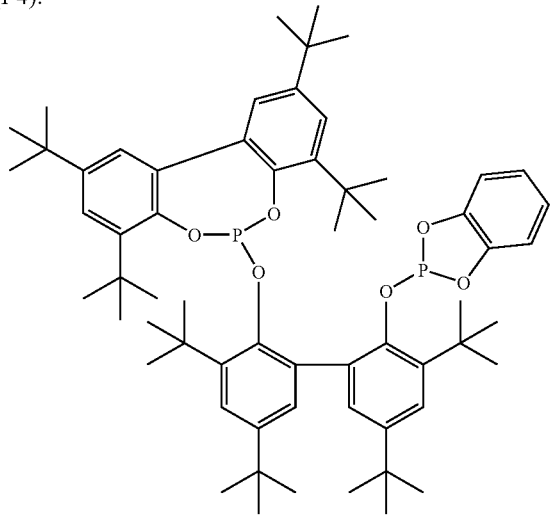

An $^1$H-NMR data of the obtained bisphosphite (I-4) is shown below.

$^1$H-NMR (270 MHz, CDCl$_3$, TMS) δ: 7.47 to 6.93 (m, 12H), 1.34 (s, 18H), 1.33 (s, 18H), 1.29 (s, 9H), 1.25 (s, 9H), 1.16 (s, 9H), 1.12 (s, 9H)

Example 6

Hydroformylation Reaction Using the Bisphosphite (I-1)

A solution of 50 mg (0.051 mmoles) of the bisphosphite (I-1) obtained in Example 2 and 20.6 mg (0.08 mmoles) of Rh(acac)(CO)$_2$ dissolved in 20 mL of toluene was prepared in a mixed gas atmosphere of carbon monoxide and hydrogen in a ratio of 1/1 (by mole), and 1 mL of such a solution was added to a toluene (4 mL) solution of 76 mg (0.077 mmoles) of the bisphosphite (I-1) at 25° C., thereby obtaining a mixed solution having a molar ratio of the rhodium atom to the phosphorus atom of 1/20 (hereinafter referred to as "catalyst solution A").

In an electromagnetic stirring type autoclave equipped with a gas inlet and a sampling port and having an inner volume of 100 mL, 2.5 mL of the catalyst solution A (corresponding to 0.002 mmoles of Rh(acac) (CO)$_2$; corresponding to 0.04 mmoles of the bisphosphite; concentration of the rhodium compound in the reaction system: 0.04 mmoles/L) and 47.5 mL (282 mmoles) of 1-methoxy-2,7-octadiene in a nitrogen atmosphere; and after substituting the inside of the autoclave with a mixed gas of carbon monoxide and hydrogen in a ratio of 1/1 (by mole) at 3 MPa (gauge pressure), the temperature in the autoclave was raised to 120° C. while stirring, and the mixture was reacted for 2 hours. During the reaction, a mixed gas of carbon monoxide and hydrogen in a ratio of 1/1 (by mole) was continually fed, thereby keeping the pressure in the reaction system constant. The obtained reaction mixture was analyzed by gas chromatography (analysis instrument: GC-17A, manufactured by Shimadzu Corporation; used column: DB-23 (60 m), manufactured by J&W Scientific; analysis condition: injection temperature at 250° C. and detection temperature at 250° C.; temperature rise condition: 100° C. (keeping for 3 minutes)→(raising the temperature at 5° C./min)→250° C. (keeping for 5 minutes). As a result, a conversion of 1-methoxy-2,7-octadiene was 93%; a selectivity of an aldehyde in which a carbon-carbon double bond in the molecular end was hydroformylated was 94%; a selectivity of a dialdehyde in which a carbon-carbon double in the molecular interior was 3%; and a rate of isomerization (proportion in which the isomerization reaction occurred in the carbon-carbon double bond) of 1-methoxy-2, 7-octadiene was 3%.

Example 7

Hydroformylation Reaction Using the Bisphosphite (I-2)

The reaction and analysis were carried out in the same manner as in Example 6, except that in Example 6, the bisphosphite (I-1) was replaced by the bisphosphite (I-2) obtained in Example 3. As a result, a conversion of 1-methoxy-2,7-octadiene was 94%; a selectivity of an aldehyde in which a carbon-carbon double bond in the molecular end was hydroformylated was 95%; a selectivity of a dialdehyde in which a carbon-carbon double in the molecular interior was 3%; and a rate of isomerization of 1-methoxy-2,7-octadiene was 2%.

Comparative Example 1

The reaction and analysis were carried out in the same manner as in Example 6, except that in Example 6, the bisphosphite (I-1) was replaced by a bisphosphite represented by the following formula.

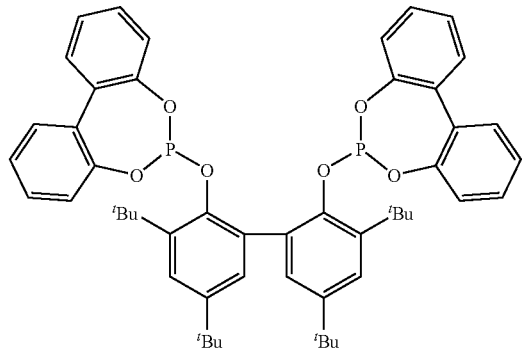

As a result, a conversion of 1-methoxy-2,7-octadiene was 91%; a selectivity of an aldehyde in which a carbon-carbon double bond in the molecular end was hydroformylated was 82%; a selectivity of a dialdehyde in which a carbon-carbon double in the molecular interior was 1%; and a rate of isomerization of 1-methoxy-2,7-octadiene was 17%.

Comparative Example 2

The reaction and analysis were carried out in the same manner as in Example 6, except that in Example 6, the bisphosphite (I-1) was replaced by a bisphosphite represented by the following formula.

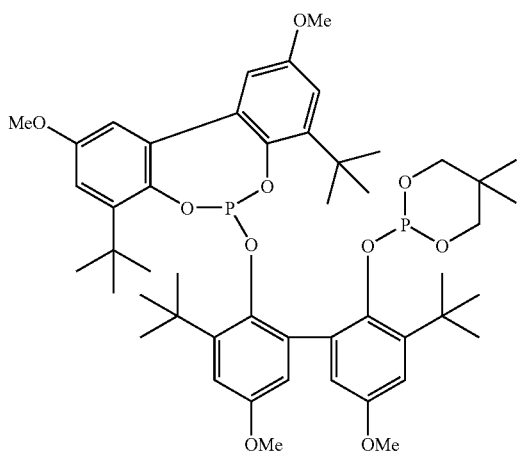

As a result, a conversion of 1-methoxy-2,7-octadiene was 93%; a selectivity of an aldehyde in which a carbon-carbon double bond in the molecular end was hydroformylated was 85%; a selectivity of a dialdehyde in which a carbon-carbon double in the molecular interior was 8%; and a rate of isomerization of 1-methoxy-2,7-octadiene was 7%.

It is noted from the results of Examples 6 and 7 and Comparative Examples 1 and 2 that when a non-conjugated diene having a carbon-carbon double bond in a molecular end and having from 6 to 20 carbon atoms is subjected to a hydroformylation reaction using the bisphosphite (I) of the present invention (Examples 6 and 7), both the hydroformylation reaction to a carbon-carbon double bond in the molecular interior and the rate of isomerization of the carbon-carbon double bond are suppressed in extremely low levels as compared with the case of using a known bisphosphite (Comparative Examples 1 and 2). On the other hand, in Comparative Example 1, though the hydroformylation reaction to the carbon-carbon double bond in the molecular interior is largely suppressed, the rate of isomerization of the carbon-carbon double bond is large as 17%. Also, in Comparative Example 2, both the hydroformylation reaction to a carbon-carbon double bond in the molecular interior and the rate of isomerization of the carbon-carbon double bond are high a little.

Test Example

In a 200-mL three-necked flask, 100 mL of toluene having a water content of 70 ppm, and 100 mg of the bisphosphite (I-1) was subsequently added, followed by substituting the inside of the system with nitrogen at room temperature. The obtained mixed solution was sealed in each of three glass tubes having an inner diameter of 8 mm under a nitrogen gas stream; and after dipping in an oil bath heated at 125° C., a rate of retention was determined every lapse of one hour by high-performance liquid chromatography (HPLC) according to an absolute calibration method. Also, the same test was carried out by using the bisphosphite (I-2), the bisphosphite (I-3) or a bisphosphite represented by the formula (II) (hereinafter referred to as "bisphosphite (II)") in place of the bisphosphite (I-1).

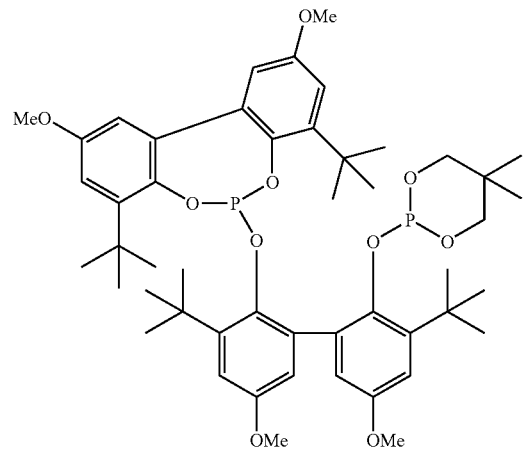

The results are collectively shown in Table 1.

[Table 1]

TABLE 1

| Lapsing time (hr) | Rate of retention | | | |
|---|---|---|---|---|
| | Bisphosphite (I-1) | Bisphosphite (I-2) | Bisphosphite (I-3) | Bisphosphite (II) |
| 0 | 100 | 100 | 100 | 100 |
| 1 | 86 | 85 | 82 | 70 |
| 2 | 78 | 78 | 74 | 52 |
| 3 | 70 | 71 | 67 | 33 |

It is noted from Table 1 that in comparison with the bisphosphite (II) which is a known phosphite and in particular, is structurally analogous to the bisphosphite of the present invention, the bisphosphite (I) of the present invention is very excellent in heat stability and resistance to hydrolysis.

The invention claimed is:

1. A method for producing an aldehyde having an aldehyde group in a molecular end, comprising reacting a non-conjugated diene having a carbon-carbon double bond in a molecular end and having from 6 to 20 carbon atoms with a carbon monoxide and hydrogen in the presence of a bisphosphite represented by the general formula (I):

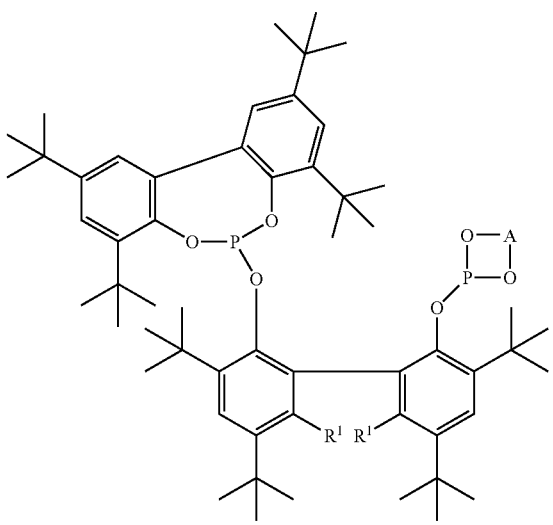

wherein A represents an alkylene group which may have a substituent, a cycloalkylene group which may have a substituent, or a phenylene group which may have a substituent; and $R^1$ represents a hydrogen atom or an alkyl group, and a group 8 to 10 metal compound.

2. The method for producing an aldehyde having an aldehyde group in a molecular end according to claim 1, wherein the non-conjugated diene having a carbon-carbon double bond in a molecular end and having from 6 to 20 carbon atoms is 1,4-hexadiene, 1-methoxy-2,7-octadiene, 1-ethoxy-2,7-octadiene, 1-propoxy-2,7-octadiene, 1-isopropoxy-2,7-octadiene, 2,7-octadien-1-ol, 1-acetoxy-2,7-octadiene or 1,6-octadiene.

3. A bisphosphite represented by the general formula (I):

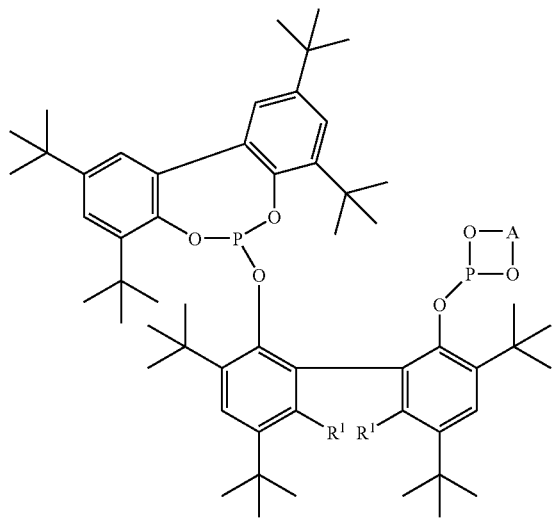

(I)

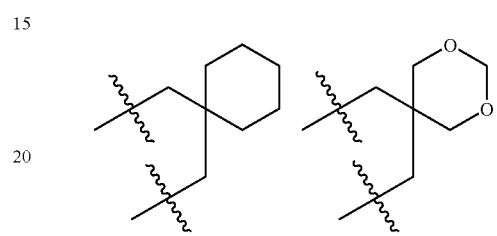

wherein A represents an alkylene group which may have a substituent, a cycloalkylene group which may have a substituent, or a phenylene group which may have a substituent, and $R^1$ represents a hydrogen atom or an alkyl group.

4. The method for producing an aldehyde having an aldehyde group in a molecular end according to claim 1, wherein the reaction is performed at a temperature of from 40 to 150° C.

5. The bisphosphite according to claim 3, wherein A is an alkylene group which may have a substituent selected from alkyl groups having from 1 to 5 carbon atoms, alkoxyl groups having from 1 to 4 carbon atoms, or aryl groups.

6. The bisphosphite according to claim 5, wherein the alkylene group is selected from an ethylene group, a trimethylene group, a tetramethylene group, a pentamethylene group, or a group represented by one of the following formulae:

wherein in the formulae, the wavy line indicates a connection site.

7. The bisphosphite according to claim 3, wherein A is a cycloalkylene group which may have a substituent selected from alkyl groups having from 1 to 5 carbon atoms, alkoxyl groups having from 1 to 4 carbon atoms, or aryl groups.

8. The bisphosphite according to claim 7, wherein the cycloalkylene group is selected from a cyclopropylene group, a 1,2-cyclopentylene group, a 1,3-cyclopentylene group, a 1,2-cyclohexylene group, a 1,3-cyclohexylene group, or a 1,4-cyclohexylene group.

9. The bisphosphite according to claim 3, wherein A is a phenylene group which may have a substituent selected from alkyl groups having from 1 to 5 carbon atoms, alkoxyl groups having from 1 to 4 carbon atoms, or aryl groups.

10. The bisphosphite according to claim 9, wherein the phenylene group is selected from a 1,2-phenylene group, a 1,3-phenylene group or a 1,4-phenylene group.

* * * * *